(12) United States Patent
Male et al.

(10) Patent No.: US 9,680,110 B2
(45) Date of Patent: Jun. 13, 2017

(54) COMPOUNDS FOR USE IN OPTO-ELECTRICAL DEVICES

(71) Applicants: CDT Oxford Limited, Cambridgeshire (GB); Sumitomo Twin Building Sumitomo Chemical Co. Limited, Tokyo (JP)

(72) Inventors: Nigel Male, Salisbury (GB); Jonathan Pillow, Baldock (GB)

(73) Assignees: CDT OXFORD LIMITED, Cambridgeshire (GB); SUMITOMO CHEMICAL CO. LIMITED, Tokyo (JP)

(*) Notice: Subject to any disclaimer, the term of this patent is extended or adjusted under 35 U.S.C. 154(b) by 0 days.

(21) Appl. No.: 14/337,202

(22) Filed: Jul. 21, 2014

(65) Prior Publication Data

US 2014/0335638 A1 Nov. 13, 2014

Related U.S. Application Data

(62) Division of application No. 12/439,163, filed as application No. PCT/GB2007/003300 on Aug. 30, 2007, now abandoned.

(30) Foreign Application Priority Data

Aug. 31, 2006 (GB) .................................. 0617167.2

(51) Int. Cl.
*H01L 51/00* (2006.01)
*C09K 11/06* (2006.01)
(Continued)

(52) U.S. Cl.
CPC ...... *H01L 51/0067* (2013.01); *C07F 15/0033* (2013.01); *C09K 11/025* (2013.01); *C09K 11/06* (2013.01); *H01L 51/0007* (2013.01); *H01L 51/0035* (2013.01); *H01L 51/0043* (2013.01); *H01L 51/0085* (2013.01);
(Continued)

(58) Field of Classification Search
None
See application file for complete search history.

(56) References Cited

U.S. PATENT DOCUMENTS 4,539,507 A 9/1985 VanSlyke et al.
5,150,006 A 9/1992 Van Slyke et al.
(Continued)

FOREIGN PATENT DOCUMENTS

EP 0 707 020 A2 4/1996
EP 0 842 208 A1 5/1998
(Continued)

OTHER PUBLICATIONS

Chen et al., "1,3,5-Triazine Derivatives as New Electron Transport-Type Host Materials for Highly Efficient Green Phosphorescent OLEDs," *J. Mater. Chem.*, 19:8112-8118 (2009).
(Continued)

*Primary Examiner* — Nathan T Leong
(74) *Attorney, Agent, or Firm* — Marshall, Gerstein & Borun LLP

(57) ABSTRACT

A composition for use in fabricating opto-electrical devices comprising a solution processable triazine host material and a phosphorescent moiety.

10 Claims, 1 Drawing Sheet

(51) Int. Cl.
  *H01L 51/50* (2006.01)
  *H05B 33/14* (2006.01)
  *C07F 15/00* (2006.01)
  *C09K 11/02* (2006.01)

(52) U.S. Cl.
  CPC ...... *H01L 51/5004* (2013.01); *H01L 51/5016* (2013.01); *H01L 51/5024* (2013.01); *H05B 33/14* (2013.01); *C09K 2211/1059* (2013.01); *C09K 2211/185* (2013.01); *H01L 51/0003* (2013.01)

(56) References Cited

U.S. PATENT DOCUMENTS

| | | | |
|---|---|---|---|
| 5,432,014 | A | 7/1995 | Sano et al. |
| 5,621,131 | A | 4/1997 | Kreuder et al. |
| 5,723,873 | A | 3/1998 | Yang |
| 5,798,170 | A | 8/1998 | Zhang et al. |
| 6,083,634 | A | 7/2000 | Shi |
| 6,225,467 | B1 | 5/2001 | Esteghamatian et al. |
| 6,268,695 | B1 | 7/2001 | Affinito |
| 6,352,791 | B1 | 3/2002 | Fink et al. |
| 6,353,083 | B1 | 3/2002 | Inbasekaran et al. |
| 6,419,172 | B1 | 7/2002 | Yamazaki et al. |
| 6,821,643 | B1 * | 11/2004 | Hu et al. ........................ 428/690 |
| 6,953,628 | B2 | 10/2005 | Kamatani et al. |
| 7,125,998 | B2 | 10/2006 | Stossel et al. |
| 7,238,435 | B2 | 7/2007 | Kamatani et al. |
| 7,250,226 | B2 | 7/2007 | Tokito et al. |
| 7,829,204 | B2 | 11/2010 | Iwakuma et al. |
| 7,883,785 | B2 | 2/2011 | Stossel et al. |
| 2002/0055014 | A1 * | 5/2002 | Okada et al. ................. 428/690 |
| 2002/0117662 | A1 | 8/2002 | Nii |
| 2002/0182441 | A1 | 12/2002 | Lamansky et al. |
| 2003/0170490 | A1 | 9/2003 | Hu et al. |
| 2004/0110031 | A1 | 6/2004 | Fukuda et al. |
| 2004/0147555 | A1 | 7/2004 | Fujimoto et al. |
| 2005/0279999 | A1 | 12/2005 | Lee et al. |
| 2005/0287393 | A1 | 12/2005 | Lee et al. |
| 2006/0099450 | A1 | 5/2006 | Ogasawara |
| 2006/0177694 | A1 | 8/2006 | Kamatani et al. |
| 2006/0180806 | A1 | 8/2006 | Arakane et al. |
| 2006/0263631 | A1 | 11/2006 | Lee et al. |
| 2006/0280964 | A1 * | 12/2006 | Liu ........................ C09K 11/06 428/690 |
| 2009/0072732 | A1 | 3/2009 | Arakane et al. |

FOREIGN PATENT DOCUMENTS

| | | |
|---|---|---|
| EP | 0 880 303 | 11/1998 |
| EP | 0 901 176 A2 | 3/1999 |
| EP | 0 947 123 A1 | 10/1999 |
| EP | 0 949 850 A1 | 10/1999 |
| EP | 1 245 659 A1 | 10/2002 |
| EP | 1281745 A1 | 2/2003 |
| EP | 1 385 221 | 1/2004 |
| EP | 1580789 A2 | 9/2005 |
| EP | 1696708 A1 | 8/2006 |
| GB | 2 348 316 A | 9/2000 |
| JP | 2002-193952 A | 7/2002 |
| JP | 2002-324679 A | 11/2002 |
| JP | 2003-335753 A | 11/2003 |
| JP | 2004-022334 | 1/2004 |
| JP | 2004-178895 A | 6/2004 |
| JP | 2005-071983 | 3/2005 |
| JP | 2005-097589 A | 4/2005 |
| JP | 2005-268022 A | 9/2005 |
| JP | 2005-536565 A | 12/2005 |
| JP | 2006-096803 A | 4/2006 |
| JP | 2006-140218 A | 6/2006 |
| JP | 2006-306783 A | 11/2006 |
| WO | WO-90/13148 A1 | 11/1990 |
| WO | WO-98/10621 | 3/1998 |
| WO | WO-98/57381 | 12/1998 |
| WO | WO-99/48160 | 9/1999 |
| WO | WO-99/48610 A1 | 9/1999 |
| WO | WO-00/48258 | 8/2000 |
| WO | WO-00/53656 A1 | 9/2000 |
| WO | WO-00/55927 A1 | 9/2000 |
| WO | WO-01/19142 A1 | 3/2001 |
| WO | WO-01/62869 A1 | 8/2001 |
| WO | WO-01/81649 A1 | 11/2001 |
| WO | WO-02/31896 A2 | 4/2002 |
| WO | WO-02/44189 | 6/2002 |
| WO | WO-02/45466 A1 | 6/2002 |
| WO | WO-02/066552 A1 | 8/2002 |
| WO | WO-02/068435 | 9/2002 |
| WO | WO-02/081448 | 10/2002 |
| WO | WO-02/083760 | 10/2002 |
| WO | WO-02/084759 A1 | 10/2002 |
| WO | WO-03/018653 | 3/2003 |
| WO | WO-03/022908 | 3/2003 |
| WO | WO-03/091355 A2 | 11/2003 |
| WO | WO-2004/060970 A1 | 7/2004 |
| WO | WO-2004/066685 A1 | 8/2004 |
| WO | WO-2004/077885 | 9/2004 |
| WO | WO-2005/029923 | 3/2005 |
| WO | WO-2005/057987 A1 | 6/2005 |
| WO | WO-2005/105950 | 11/2005 |

OTHER PUBLICATIONS

Chen et al., "Recent Developments in Molecular Organic Electroluminescent Materials," *Macromol. Symp.*, 125:1-48 (1997).
Chen et al., "Triplet exciton confinement in phosphorescent polymer light-emitting diodes," *Applied Physics Letters*, 82:1006-1008 (2003).
Cleave et al., "Harvesting Singlet and Triplet Energy in Polymer LEDs," *Adv. Matter*, 11:285-288 (1999).
English translation of Office Action for corresponding Korean Patent Application No. 2009-7006304, dated Dec. 24, 2013.
Gardette et al., "Investigation of the Photophysical Processes and Photochemical Reactions Involved in PVK Films Irradiated at Lambda > 300," *Macromolecules*, 36:5815-5824 (2003).
Ikai et al., "Highly efficient phosphorescence from organic light-emitting devices with an exciton-block layer," *Applied Physics Letters*, 79:156-158 (2001).
Inomata et al., "High-Efficiency Organic Electrophosphorescent Diodes Using 1,3,5-Triazine Electron Transport Materials," *Chem. Materials*, 16:1285-1291 (2004).
International Preliminary Report on Patentability for PCT/GB2007/003300, dated Mar. 3, 2009.
International Search Report for PCT/GB2007/003300 dated Dec. 11, 2007.
Jin et al., "Photoconductive Properties of PVK:Alq3 Blend Films Studied by Steady-State and Time-Resolved Transient Photocurrent Spectra," Chinese, *J. Polymer Sci.*, 26(3):249-254 (2008).
Lamansky et al., "Molecularly Doped Polymer Light Emitting Diodes Utilizing Phosphorescent (Pt(II) and Ir(III) Dopants," *Organic Electronics*, 2:53-63 (2001).
Lane et al., "Origin of Electrophosphorescence from a Doped Polymer Light Emitting Diode," *Phys. Rev. B.*, 63:235206-1-236206-8 (2001).
Lee et al., "Polymer phosphorescent light-emitting devices doped with tris(2-phenylpyridine) iridium as a triplet emitter," *Applied Physics Letters*, 77:2280-2282 (2000).
Niu et al., "Thermal annealing below the glass transition temperature: A general way to increase performance of light-emitting diodes based on copoyfluorenes," *Applied Physics Letters*, 81:634-636 (2002).
O'Brien et al., "Electrophosphorescence from a doped polymer light emitting diode," *Synthetic Metals*, 116:379-383 (2001).
Office Action for corresponding Japanese Patent Application No. 2009-526176, dated Oct. 6, 2012 (Partial English Translation).
Partial English translation of Office Action for corresponding Japanese Patent Application No. 2009-526176, dated Oct. 8, 2013.
Setayesh et al., "Bridging the Gap between Polyfluorene and Ladder-Poly-p-phenylene: Synthesis and Characterization of Poly-2,8-indenofluorene," *Macromolecules*, 33:2016-2020 (2000).

(56) References Cited

OTHER PUBLICATIONS

Sudhakar et al., "Phosphorescence Quenching by Conjugated Polymers," *J. Am. Chem. Soc. (JACS)*, 125:7796-7797 (2003).
Third Party Observation Pursuant to Article 115 EPC filed in corresponding European Patent Application No. 07804106.8, dated Oct. 8, 2012.
Tokito et al., "Metal oxides as a hole-injecting layer for an organic electroluminescent device," *J. Physics D*, 29:2750-2753 (1996).
Yamaguchi et al., "Effects of B and C on the Ordering of L10-CoPt thin films," *Applied Physics Letters*, 79:2001-2003 (2001).
Yamamoto, "Electrically Conducting and Thermally Stable π-Conjugated Poly (arylene)s Prepared by Organometallic Processes," *Prog. Polym. Sci.*, 17:1153-1205 (1992).
Yang, "Efficient blue polymer light-emitting diodes from a series of soluble poly(paraphenylene)s," *J. Appl. Phys.*, 79:934-939 (1996).
Zhu et al., "Synthesis of new iridium complexes and their electrophosphorescent properties in polymer light-emitting diodes," *J. Mater. Chem.*, 13:50-55 (2003).
Vaeth et al., "Light-Emitting Diodes Based on Phosphorescent Guest/Polymeric Host Systems," *J. Appl. Phys.*, 92(7):3447-3453 (2002).
Notification of Reasons for Refusal (with machine translation), Japanese patent application No. 2015-062158, mailed Oct. 11, 2016.

\* cited by examiner

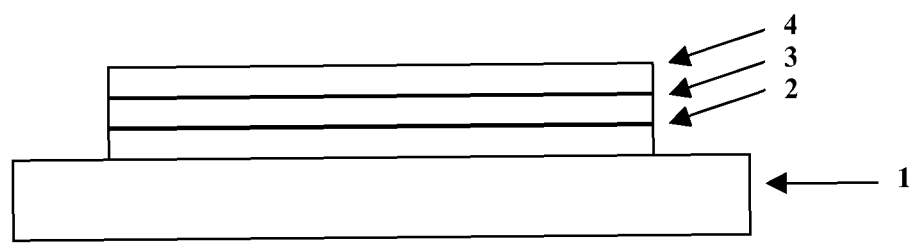

COMPOUNDS FOR USE IN OPTO-ELECTRICAL DEVICES

FIELD OF INVENTION

This invention relates to compositions comprising triazine host compounds for use in fabricating phosphorescent opto-electrical devices, and methods of fabricating opto-electrical devices using these compositions.

BACKGROUND OF INVENTION

One class of opto-electrical devices is that using an organic material for light emission or detection. The basic structure of these devices is a light emissive organic layer, for instance a film of a poly (p-phenylenevinylene) ("PPV") or polyfluorene, sandwiched between a cathode for injecting negative charge carriers (electrons) and an anode for injecting positive charge carriers (holes) into the organic layer. The electrons and holes combine in the organic layer generating photons. In WO 90/13148 the organic light-emissive material is a polymer. In U.S. Pat. No. 4,539,507 the organic light-emissive material is of the class known as small molecule materials, such as (8-hydroxyquinoline) aluminium ("Alq3"). In a practical device one of the electrodes is transparent, to allow the photons to escape the device.

A typical organic light-emissive device ("OLED") is fabricated on a glass or plastic substrate coated with a transparent first electrode such as indium-tin-oxide ("ITO"). A layer of a thin film of at least one electroluminescent organic material covers the first electrode. Finally, a cathode covers the layer of electroluminescent organic material. The cathode is typically a metal or alloy and may comprise a single layer, such as aluminium, or a plurality of layers such as calcium and aluminium. Other layers can be added to the device, for example to improve charge injection from the electrodes to the electroluminescent material. For example, a hole injection layer such as poly (ethylene dioxythiophene)/polystyrene sulfonate (PEDOT-PSS) or polyaniline may be provided between the anode and the electroluminescent material. When a voltage is applied between the electrodes from a power supply one of the electrodes acts as a cathode and the other as an anode.

In operation, holes are injected into the device through the anode and electrons are injected into the device through the cathode. The holes and electrons combine in the organic electroluminescent layer to form an exciton which then undergoes radiative decay to give light.

For organic semiconductors, important characteristics are the binding energies, measured with respect to the vacuum level of the electronic energy levels, particularly the "highest occupied molecular orbital" (HOMO) and the "lowest unoccupied molecular orbital" (LUMO) level. These can be estimated from measurements of photoemission and particularly measurements of the electrochemical potentials for oxidation and reduction. It is well understood in this field that such energies are affected by a number of factors, such as the local environment near an interface, and the point on the curve (peak) from which the value is determined. Accordingly, the use of such values is indicative rather than quantitative.

The optical and electronic properties of an organic semiconductor are highly dependent on the energy of the aforementioned HOMO and LUMO levels. Furthermore, these energy levels are highly dependent on the chemical structure of the organic semiconductor. By selecting suitable materials, or combinations of materials, device performance can be improved.

For example, one way of improving efficiency of devices is to provide hole and electron transporting materials. WO 99/48610 discloses blending of hole transporting polymers, electron transporting polymers and electroluminescent polymers. A 1:1 copolymer of dioctylfluorene and triphenylamine is disclosed as a hole transporting polymer in this document. The type of charge transporting material which is most effective will be dependent on the HOMO and LUMO of the other components in the device.

Although there has been much improvement in the efficiency of devices using charge transporting materials, there is always a desire to develop new charge transporting materials to further improving efficiency when compared with existing devices.

WO 02/083760 discloses copolymers for use as charge transporting materials and fluorescent emissive materials in organic opto-electrical devices. The co-polymers comprise a first repeat unit which may be a triazine unit as shown in formula (a):

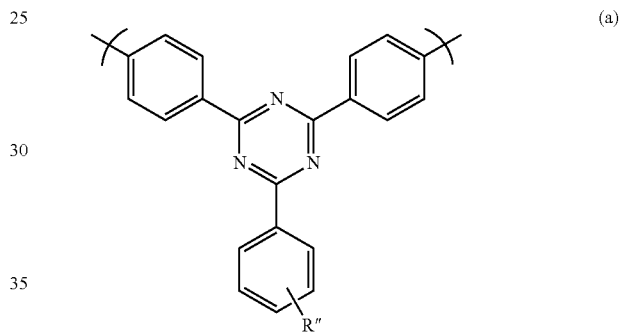

wherein R" is selected from hydrogen, branched or linear C1-C20 alkyl or alkoxy.

The copolymers comprise a second repeat unit which may be selected from the group consisting of optionally substituted phenylenes, fluorenes, heteroaryls and triarylamines.

Triazines as components of blue electroluminescent devices are disclosed in WO 2004/077885.

U.S. Pat. No. 6,821,643 discloses arylated triazines that are deposited by evaporation to form a blue fluorescent light-emitting layer or an electron transport layer of an OLED.

U.S. Pat. No. 6,352,791 discloses arylated triazines that are deposited by evaporation to form an electron transport layer of an OLED.

WO 2005/105950 discloses certain tri-substituted triazines used as a blue fluorescent light-emitting layer of an OLED.

EP 1385221 discloses a light-emitting device comprising a luminescent region comprising an anthracene derivative compound and a triazine derivative compound.

Phosphorescent materials are also useful and in some applications may be preferable to fluorescent materials. One type of phosphorescent material comprises a host and a phosphorescent emitter in the host. The emitter may be bonded to the host or provided as a separate component in a blend.

Numerous hosts for phosphorescent emitters are described in the prior art including "small molecule" hosts such as 4,4'-bis(carbazol-9-yl)biphenyl), known as CBP, and (4,4',4"-tris(carbazol-9-yl)triphenylamine), known as TCTA, disclosed in Ikai et al. (*Appl. Phys. Lett.,* 79 no. 2, 2001, 156); and triarylamines such as tris-4-(N-3-methyl-phenyl-N-phenyl)phenylamine, known as MTDATA. Homopolymers are also known as hosts, in particular poly(vinyl carbazole) disclosed in, for example, Appl. Phys. Lett. 2000, 77(15), 2280; polyfluorenes in Synth. Met. 2001, 116, 379, Phys. Rev. B 2001, 63, 235206 and Appl. Phys. Lett. 2003, 82(7), 1006; poly[4-(N-4-vinylbenzyloxyethyl, N-methylamino)-N-(2,5-di-tert-butylphenylnapthalimide] in Adv. Mater. 1999, 11(4), 285; and poly(para-phenylenes) in J. Mater. Chem. 2003, 13, 50-55.

A problem with known host-phosphor systems is that the host may quench emission from the phosphor. In general, the lower the triplet energy level of the host (relative to the phosphor) then the more likely quenching will occur. Polymerisation can exacerbate this problem by reducing the triplet energy level to below that of a monomer when forming a host polymer. Accordingly, there is a need to produce materials with a high triplet energy level for use as hosts in phosphorescent systems.

JP 2005071983 discloses tris-carbazolyl substituted triazines as a host for Irppy, for example:

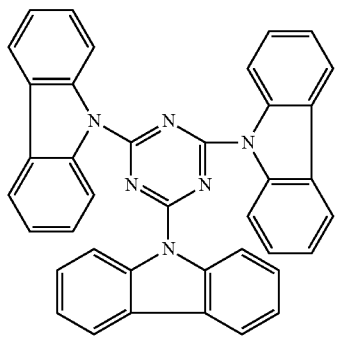 [SMILES: c1ccc2c(c1)c1ccccc1n2-c1nc(-n2c3ccccc3c3ccccc32)nc(-n2c3ccccc3c3ccccc32)n1]

In Chemistry of Materials (2004), 16(7), 1285-1291 a tris-carbazolyl compound and other arylamino-substituted triazines are disclosed as hosts for Irppy in OLEDs, for example:

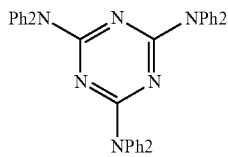

WO 2005029923 discloses tris-benzimidazolyl substituted triazine as a host for the red phosphor, Ir (piq):

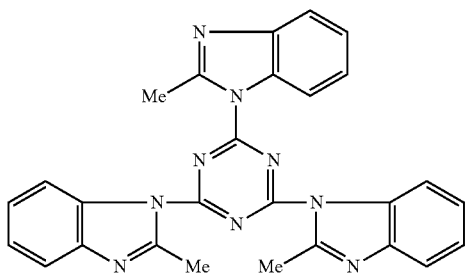 [SMILES: Cc1nc2ccccc2n1-c1nc(-n2c(C)nc3ccccc32)nc(-n2c(C)nc3ccccc32)n1]

US2005/0287393 discloses a light emissive composition comprising a phosphorescent dopant and a host including a carbazole compound and a small molecule triazine compound. Exemplary triazine compounds are given as 2,4,6-tris(diarylamino)-1,3,5-triazine, 2,4,6-tris(diphenylamino)-1,3,5-triazine, 2,4,6-tricarbazolo-1,3,5-triazine, 2,4,6-tris(N-phenyl-2-naphthylamino)-1,3,5-triazine, 2,4,6-tris(N-pheyl-1-naphthyl amino)-1,3,5-triazine, or 2,4,6-trisbiphenyl-1,3,5-triazine.

All of the above-identified small molecule triazines for use as hosts in phosphorescent compositions are amino derivative except for the last example, 2,4,6-trisbiphenyl-1,3,5-triazine, given in the list of examples in US2005/0287393. The amino derivatives all have a nitrogen atom directly bonding the aryl substituents to the central triazine ring. However, the present applicant proposes that this nitrogen linkage is not completely stable which can reduce the lifetime of these compositions. Furthermore, none of the above-identified small molecule compounds are soluble enough to be readily solution processed and instead these compounds are more suited to vacuum thermal deposition.

Host-emitter systems are not limited to phosphorescent devices. A wide range of fluorescent low molecular weight metal complexes are known and have been demonstrated in organic light emitting devices [see, e.g., Macromol. Sym. 125 (1997) 1-48, U.S. Pat. Nos. 5,150,006, 6,083,634 and 5,432,014].

As with phosphorescent systems, a problem with known host-fluorescent emitter systems is that the host may quench emission from the fluorescent emitter. It is advantageous to provide a host having a higher LUMO than that of the emitter to inject electrons into the emitter. It is advantageous to provide a host having a lower HOMO than that of the emitter to inject holes into the emitter. Accordingly, there is a need to produce materials with a large band gap between the HOMO and LUMO for use as hosts in fluorescent systems.

Another factor affecting the performance of opto-electronic devices is morphology of the films which make up the device. For semiconductive organic materials it is advantageous to have an amorphous rather than a crystalline film. However, it is desirable not to have too much disorder in the film in order to achieve a device with better performance. Accordingly, there is a desire to produce materials with better film forming characteristics.

It is an aim of the present invention to solve one or more of the problems outlined above.

SUMMARY OF THE PRESENT INVENTION

According to a first aspect of the present invention there is provided a composition for use in fabricating opto-electrical devices comprising a solution processable triazine host material and a phosphorescent moiety.

In one embodiment, the solution processable triazine host material is a small molecule triazine compound.

In another embodiment, the solution processable triazine host material is a polymer comprising a triazine repeat unit.

By "small molecule" we mean non-polymeric. The term "small molecule" is often used in this art to have this meaning as there are two main families of organic opto-electrical materials: polymers and small molecules. Oligomers consist of 1 to 10 repeat units, more preferably, 1 to 5 repeat units.

Preferably, the triazine host material comprises a solubilising substituent.

By "solubilizing substituent" we mean a substituent which renders the triazine sufficiently soluble in organic solvents that it can be solution processed to fabricate an opto-electrical device by, for example, ink-jet printing or spin-coating. Generally, compounds must be soluble to a concentration above 8 mg ml$^{-1}$, preferably above 10 mg ml$^{-1}$, in order for them to be solution processed in a device manufacturing method. Organic solvents suitable for opto-electrical device fabrication include xylene, toluene, chlorobenzene, chloroform or tetrahydrofuran but preferably toluene or xylene. The prior art compound 2,4,6-tris(biphenyl)-1,3,5-triazine has a solubility <5 mg ml$^{-1}$ in all of these solvents and thus is not a suitable material for fabricating an OLED device by solution processing.

It has been found that by providing a solubilising substituent on a small molecule triazine compound, the compound can be readily solution processed. As such, the compositions comprising small molecule triazine compounds of the present invention can be deposited to form a film by, for example, ink-jet printing or spin-coating rather than thermal vapour deposition.

Furthermore, it has been found that solubilising substituents reduce the crystallinity of a film formed by depositing triazine compounds when compared with prior art small molecule triazine compounds resulting in a better film morphology. In addition, the solubilizing substituent can be used to tune the physical properties of a film.

Thus, the present invention provides triazine compounds which can be solution processed and which produce films having a good morphology and tunable physical properties for use in opto-electrical devices. Furthermore, the triazine compounds of the present invention have both a deep LUMO and a deep HOMO. As such, the triazine compounds readily accept electrons but do not readily accept holes in an opto-electrical device. Moreover, these compounds serve as electron transporting host materials for emissive materials without quenching emission from the emissive materials. Preferably, the LUMO level is intermediate in energy between the fermi level of the electron injecting material in the cathode and the LUMO level (or triplet level in phosphorescent emissive materials) of the emissive material or at least not significantly higher than the fermi level of the electron injecting material or significantly lower than the LUMO (or triplet level) of the emissive material as to require a high drive voltage. Preferably, the HOMO level of the triazine compounds is lower than the HOMO level of the emissive material. Due to the poor hole accepting/hole transporting properties of the triazines, it is preferable to use them in conjunction with a hole transporting material or with an emissive material which is a good hole transporting material.

The LUMO levels of the triazine compounds are preferably intermediate in energy between the injecting cathode and the emitter. If a barrier to electron injection is present it is preferably not more than 0.4 eV above the work function of the cathode. The HOMO level of the triazine should be such as to maintain an optical band-gap large enough to maintain a triplet level energy gap that will not quench the phosphorescence from the emitter species.

The electrical characteristics of the triazine compounds of the present invention are such that in additional to acting as good host materials, they can also be used as blue emissive materials, electron transporting materials (either in a separate electron transporting layer located between the cathode and the emissive layer of a device or incorporated into the emissive layer of the device as a blend with an emissive material or bonded to the emissive material) and/or hole blocking materials (located in a layer between the emissive layer and the cathode in a device). Furthermore, the low LUMO of the triazine compounds also allows cathode materials with higher work-functions to be used. Triazine compounds with LUMO level of, for example, 2.8 eV will allow the use of higher work function cathodes where the energy gap is not greater than 0.4 eV. Thus cathode materials with work functions in the range 2.6 to 3.2 eV are preferred.

Preferably, the at least one solubilizing substituent comprises a $C_4$-$C_{20}$ alkyl chain. It has been found that alkyl chains within this range render the triazine compound sufficiently soluble to be readily solution processed and form films having a good morphology. The length and composition of the alkyl chain can be tailored to tune the physical properties of the film according to its specific use.

Preferably, the central triazine ring is substituted with at least one aryl group. Most preferably, the aryl group is directly bonded to the central triazine ring. The aryl group may be a phenyl ring. Most preferably, the triazine compound is a tris-aryl triazine with at least one of the aryl groups having a solubilizing substituent bonded thereto. More preferably, two or three of the aryl groups have solubilizing substituents bonded thereto. The solubilizing groups may be the same or different.

It has been found that tris-aryl triazine compounds having solubilizing groups thereon form films with a good physical morphology and good physical properties. In particular, the aryl groups and the solubilising groups provide a film which is amorphous but does not have too much disorder. These films have better opto-electrical properties and produce a device with better performance.

Preferably, the at least one solubilizing substituent is directly bonded to the central triazine ring via a carbon atom. As previously stated, the prior art triazine compounds which have substituents bonded to the central triazine ring via a nitrogen atom may be unstable in an opto-electrical device thus reducing the lifetime of the device. The nitrogen linking atom may act as a reactive site for substitution of the substituent during device operation. In contrast, carbon bonded substituents according to embodiments of the present invention are more stable in an opto-electrical device.

According to embodiments of the present invention, the triazine structures are simple triaryl substituted compounds without heteroatom linkages but with alkyl substituents or preferably aryl substituents having alkyl groups thereon, selected to allow tuning of the physical properties of the films formed using these structures, e.g. Tg>150° C., good film morphology, appropriate HOMO and LUMO levels etc. An example of such a structure is shown in the formula below:

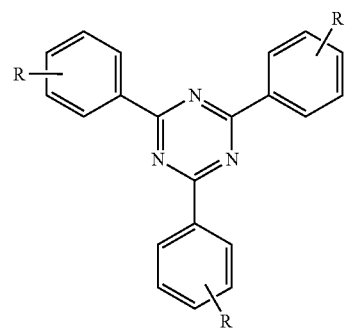

where the R groups are solubilizing substituents. Asymmetric structures where R on one ring can differ from R on the other two rings are also possible. Further examples are given in the formulas below:
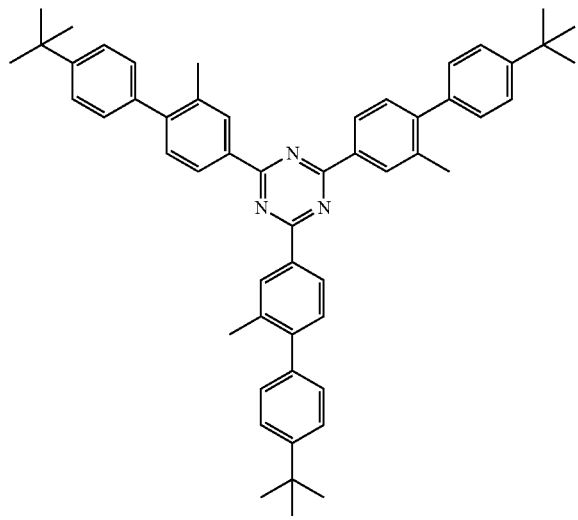
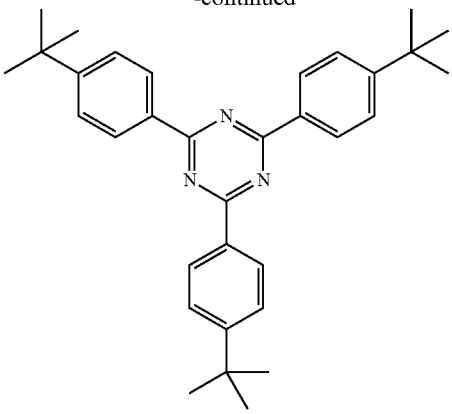
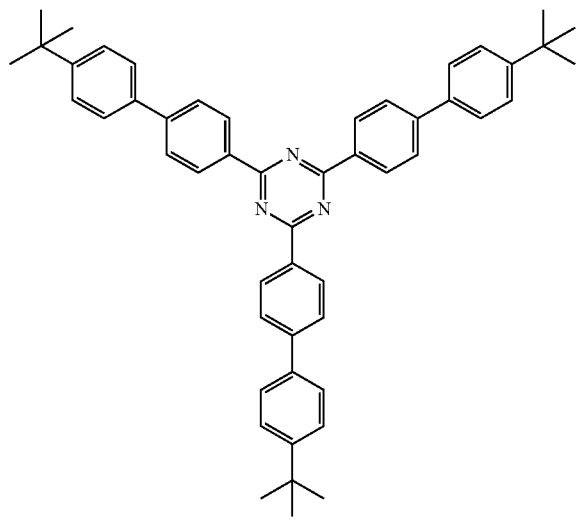
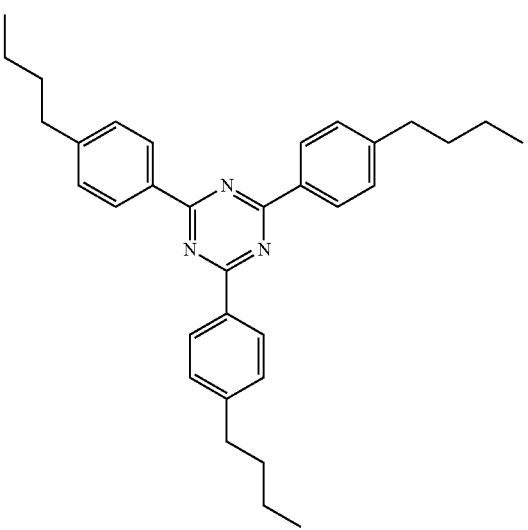
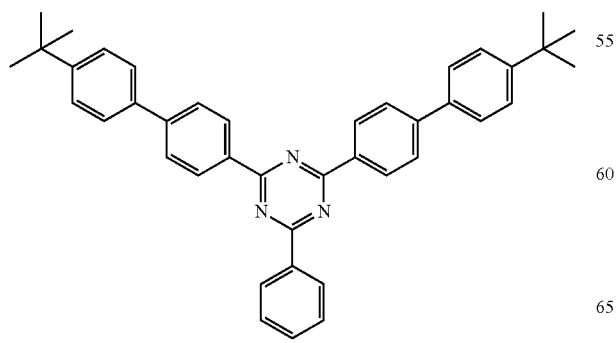
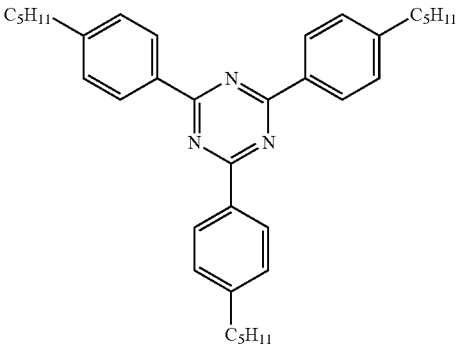

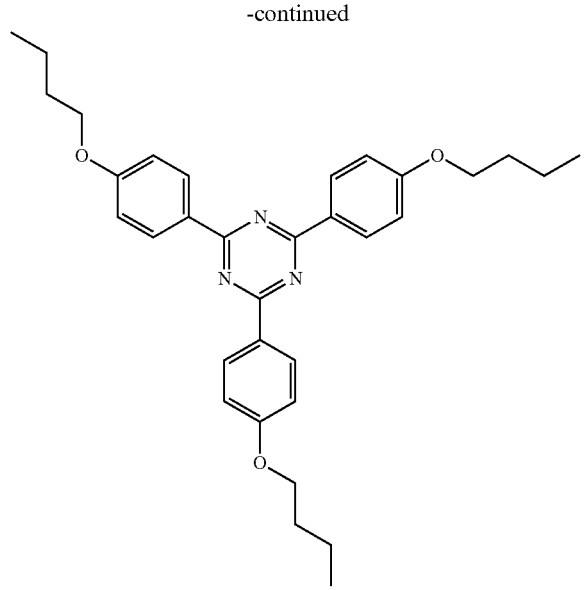
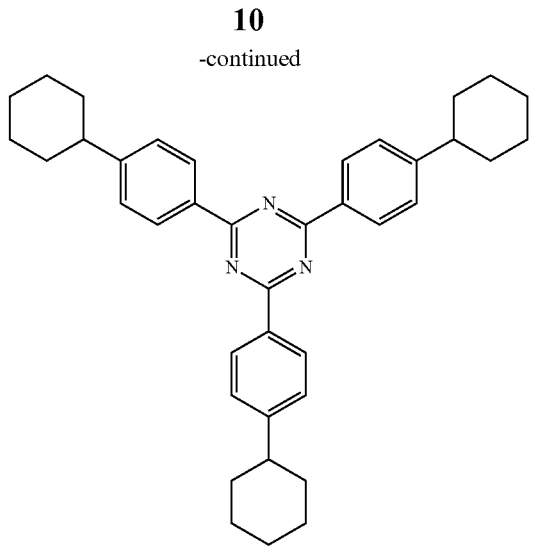
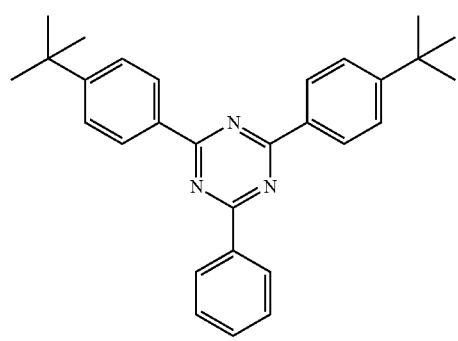
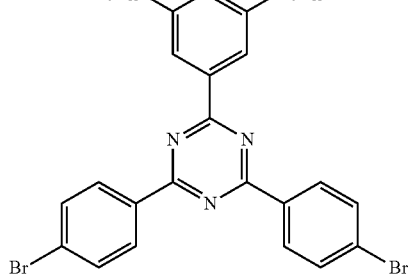
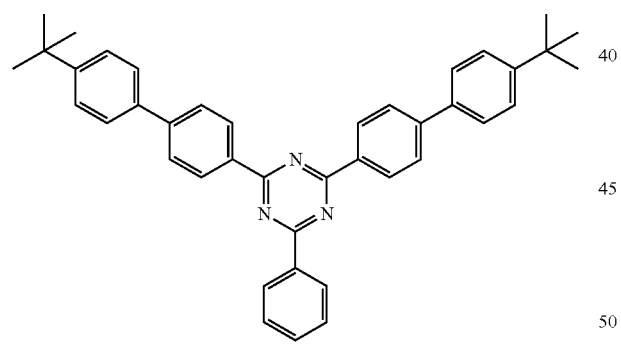
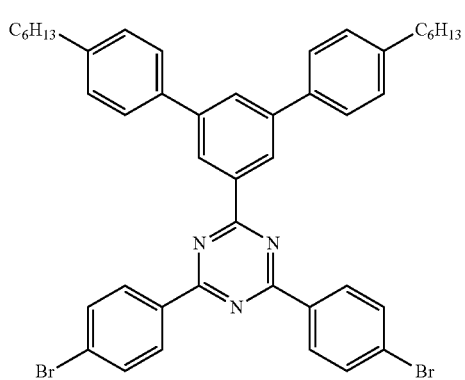
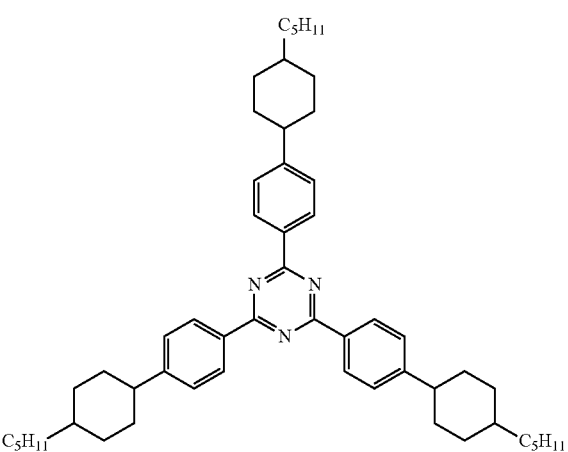

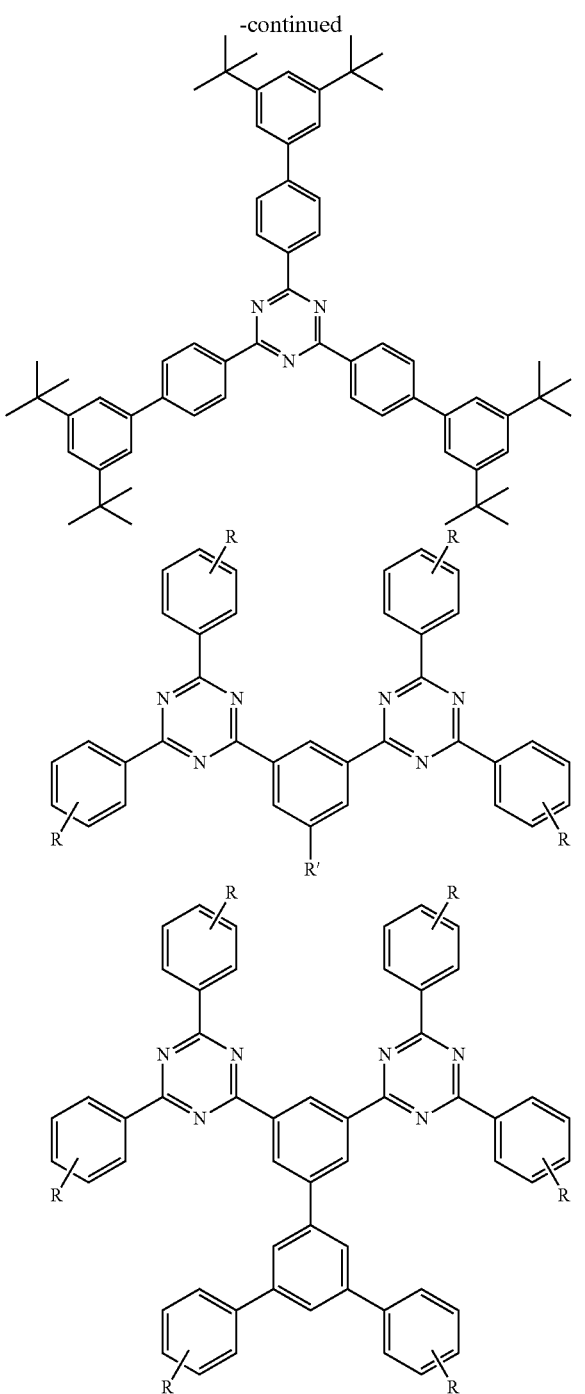

The specific compounds shown above have been device tested as host materials for green phosphorescent materials and exhibit superior lifetime performance to known solution processable green hosts. It is also envisaged that embodiments of the present invention may be utilized as hosts for red phosphorescent materials.

It is believed that the triphenyl triazine moiety that is common to the above structures is more chemically and electrochemically inert and is therefore more stable in the device when compared with standard hosts, for example CBP, optionally substituted with solubilising groups such as alkyl or alkoxy groups. The triazines are also advantageous as they have good electron transport properties, which make them much more suitable for use in common device structures, as they can be used in conjunction with an electron-blocking/hole transporting layer disposed between the light-emissive layer and a hole injecting layer. There is also no need for a hole-blocking/electron transporting layer disposed between the light-emissive layer and the cathode, which is commonly required in phosphorescent devices.

One potential problem with the compounds shown above is that their energy levels might be too deep for some applications. However, with appropriate substitution (with e.g. amines) optimum energy levels can be obtained for these applications. It should be noted that amine substituents should not be directly bonded to the central triazine ring via a nitrogen atom for the reasons discussed previously. Alternatively any other functional groups with suitable electron donating or electron withdrawing groups may be used as required including but not limited to for example Fluoro-aryl, perfluoro-aryl, alkyl-aryl or alkoxy-aryl groups.

It has been found that solution processable triazine materials are excellent hosts for phosphorescent emissive materials as their deep LUMO provide enhanced electron-injection/transport and their wide triplet band-gap reduces quenching. The advantageous features described in relation to the first aspect of the invention are also applicable to the second aspect of the invention.

The triazine units may be provided in a copolymer with, for example, hole transporting units such as a triaryl amine or a twisted co-monomer which will maintain the triplet level of the polymer so as not to quench the emission from the phosphorescent emitter. For example,

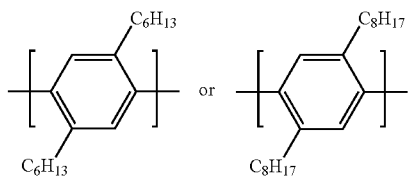

Alternatively, or additionally, the co-polymer may comprise the phosphorescent moiety. The phosphorescent moiety may be provided in the polymer backbone or in a pendent side chain.

Preferably the phosphorescent moiety is a green emitter. Known hosts for green emitters such as solution processable polyfluorene host materials generally have triplet levels that are too low to be efficient hosts for green phosphorescent moieties. In contrast, embodiments of the present invention are efficient host materials for green phosphorescent moieties. However, it is envisaged that the solution processable triazines may also be used as hosts for red phosphorescent moieties.

An example of a triazine monomer suitable for fabricating polymer hosts is shown below:

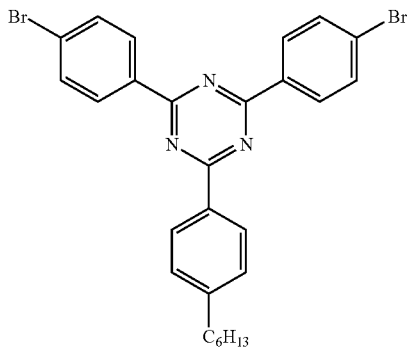

As a host material for green phosphorescence, these monomers can be used to prepare wide band-gap polymers with similarly good electron injection/transport, but that avoid the need for polyfluorenes that generally have triplet levels that are too low to use as a green phosphorescent host. For example:

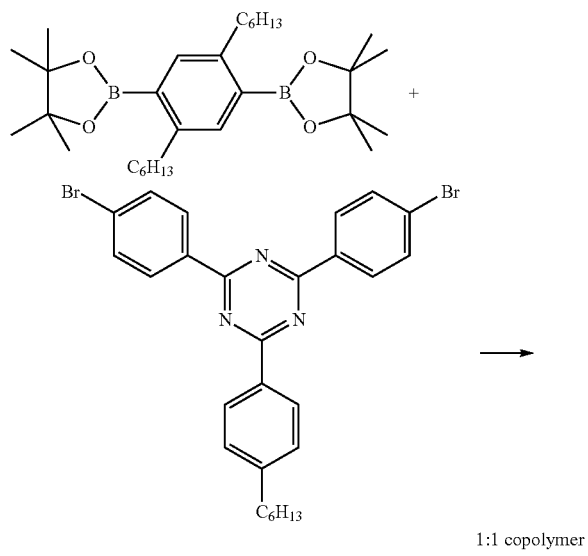

1:1 copolymer

This polymer has the processing properties of a conjugated polymer with the triplet band-gap and electron injection properties of the triazine. Other monomers could also be introduced to fine-tune the charge injection/conduction properties, or to add luminescent centres.

According to a third aspect of the present invention there is provided a method of fabricating an opto-electrical device, the method comprising the steps: depositing from solution, on a substrate comprising a first electrode for injecting charge carriers of a first polarity, a composition according to the first aspect of the present invention; and depositing thereover a second electrode for injecting charge carriers of a second polarity opposite to the first polarity.

According to a fourth aspect of the present invention there is provided an opto-electrical device comprising: a substrate; a first electrode disposed over the substrate for injecting charge carriers of a first polarity; a layer disposed over the first electrode comprising a composition according to the first aspect of the present invention; and a second electrode disposed thereover for injecting charge carriers of a second polarity opposite to the first polarity.

BRIEF DESCRIPTION OF THE DRAWINGS

Embodiments of the present invention will now be described by way of example only with reference to the accompanying drawing in which:

FIG. 1 shows an organic light emitting device according to an embodiment of the present invention.

DETAILED DESCRIPTION OF EMBODIMENTS OF THE INVENTION

The device shown in FIG. 1 comprises a transparent glass or plastic substrate 1, an anode 2 of indium tin oxide and a cathode 4. An electroluminescent layer 3 is provided between anode 2 and cathode 4.

Further layers may be located between anode 2 and cathode 3, such as charge transporting, charge injecting or charge blocking layers.

In particular, it is desirable to provide a conductive hole injection layer formed of a doped organic material located between the anode 2 and the electroluminescent layer 3 to assist hole injection from the anode into the layer or layers of semiconducting polymer. Examples of doped organic hole injection materials include: poly(ethylene dioxythiophene) (PEDT), in particular PEDT doped with a charge-balancing polyacid such as polystyrene sulfonate (PSS) as disclosed in EP 0901176 and EP 0947123, polyacrylic acid or a fluorinated sulfonic acid, for example Nafion®; polyaniline as disclosed in U.S. Pat. Nos. 5,723,873 and 5,798,170; and poly(thienothiophene). Conductive inorganic materials may also be employed as hole injection layers. Suitable inorganic materials include transition metal oxides such as VOx MoOx and RuOx as disclosed in Journal of Physics D: Applied Physics (1996), 29(11), 2750-2753.

If present, a hole transporting layer located between anode 2 and electroluminescent layer 3 preferably has a HOMO level of less than or equal to 5.5 eV, more preferably around 4.8-5.5 eV.

If present, an electron transporting layer located between electroluminescent layer 3 and cathode 4 preferably has a LUMO level of around 3-3.5 eV.

Electroluminescent layer 3 may consist of the electroluminescent material alone or may comprise the electroluminescent material in combination with one or more further materials. In particular, the electroluminescent material may be blended with hole and/or electron transporting materials as disclosed in, for example, WO 99/48160. Alternatively, the electroluminescent material may be covalently bound to a charge transporting material.

Cathode 4 is selected from materials that have a workfunction allowing injection of electrons into the electroluminescent layer. Other factors influence the selection of the cathode such as the possibility of adverse interactions between the cathode and the electroluminescent material. The cathode may consist of a single material such as a layer of aluminium. Alternatively, it may comprise a plurality of metals, for example a bilayer of a low workfunction material and a high workfunction material such as calcium and aluminium as disclosed in WO 98/10621, elemental barium disclosed in WO 98/57381, Appl. Phys. Lett. 2002, 81(4), 634 and WO 02/84759 or a thin layer of metal compound, in particular an oxide or fluoride of an alkali or alkali earth metal, to assist electron injection, for example lithium fluoride disclosed in WO 00/48258; barium fluoride, disclosed in Appl. Phys. Lett. 2001, 79(5), 2001; and barium oxide. In order to provide efficient injection of electrons into the device, the cathode preferably has a workfunction of less than 3.5 eV, more preferably less than 3.2 eV, yet more preferably less than 3 eV, most preferably less than 2.8 eV.

Optical devices tend to be sensitive to moisture and oxygen. Accordingly, the substrate preferably has good barrier properties for prevention of ingress of moisture and oxygen into the device. The substrate is commonly glass, however alternative substrates may be used, in particular where flexibility of the device is desirable. For example, the substrate may comprise a plastic as in U.S. Pat. No. 6,268,695 which discloses a substrate of alternating plastic and barrier layers or a laminate of thin glass and plastic as disclosed in EP 0949850.

The device is preferably encapsulated with an encapsulant (not shown) to prevent ingress of moisture and oxygen. Suitable encapsulants include a sheet of glass, films having suitable barrier properties such as alternating stacks of polymer and dielectric as disclosed in, for example, WO 01/81649 or an airtight container as disclosed in, for example, WO 01/19142. A getter material for absorption of any atmospheric moisture and/or oxygen that may permeate through the substrate or encapsulant may be disposed between the substrate and the encapsulant.

In a practical device, at least one of the electrodes is semi-transparent in order that light may be absorbed (in the case of a photoresponsive device) or emitted (in the case of an OLED). Where the anode is transparent, it typically comprises indium tin oxide. Examples of transparent cathodes are disclosed in, for example, GB 2348316.

The embodiment of FIG. 1 illustrates a device wherein the device is formed by firstly forming an anode on a substrate followed by deposition of an electroluminescent layer and a cathode. However it will be appreciated that the device of the invention could also be formed by firstly forming a cathode on a substrate followed by deposition of an electroluminescent layer and an anode.

Semiconductive polymers may be provided for the purpose of charge transport, emission or as host polymers. A range of repeat units for such polymers are described in more detail below. These polymers may be used separately from the triazines of the present invention (for example as a separate emissive centre in a multicolour device).

Alternatively, these repeat units may be used in combination with the triazines. For example, the solution processable triazine host material according to the second aspect of the invention may comprise a triazine repeat unit and one or more further repeat units selected from those described below. In this case, it will be appreciated that the polymer formed from such repeat units used in combination with the triazine repeat units must have a triplet energy higher than that of the phosphorescent dopant.

Polymers may comprise a first repeat unit selected from arylene repeat units, in particular: 1,4-phenylene repeat units as disclosed in J. Appl. Phys. 1996, 79, 934; fluorene repeat units as disclosed in EP 0842208; indenofluorene repeat units as disclosed in, for example, Macromolecules 2000, 33(6), 2016-2020; and spirofluorene repeat units as disclosed in, for example EP 0707020. Each of these repeat units is optionally substituted. Examples of substituents include solubilising groups such as $C_{1-20}$ alkyl or alkoxy; electron withdrawing groups such as fluorine, nitro or cyano; and substituents for increasing glass transition temperature (Tg) of the polymer.

Polymers may comprise optionally substituted, 2,7-linked fluorenes, for example repeat units of formula:

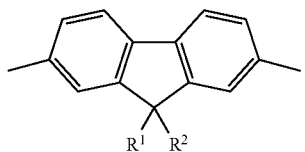

wherein $R^1$ and $R^2$ are independently selected from hydrogen or optionally substituted alkyl, alkoxy, aryl, arylalkyl, heteroaryl and heteroarylalkyl. More preferably, at least one of $R^1$ and $R^2$ comprises an optionally substituted $C_4$-$C_{20}$ alkyl or optionally substituted aryl group.

Polymers may provide one or more of the functions of hole transport, electron transport and emission depending on which layer of the device it is used in and the nature of co-repeat units.

In particular:
  a homopolymer of fluorene repeat units, such as a homopolymer of 9,9-dialkylfluoren-2,7-diyl, may be utilised to provide electron transport.
  a polymer, preferably a copolymer, comprising a triarylamine repeat unit, in particular a repeat unit selected from formulae 1-6, may be utilised to provide hole transport and/or emission of a different colour to that of the composition of the invention:

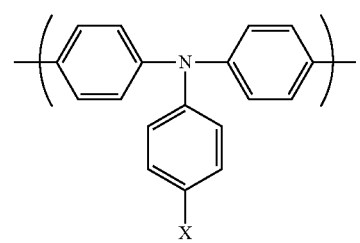

1

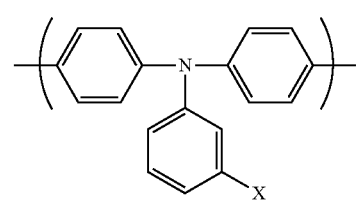

2

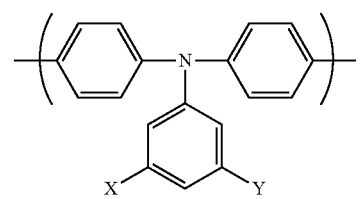

3

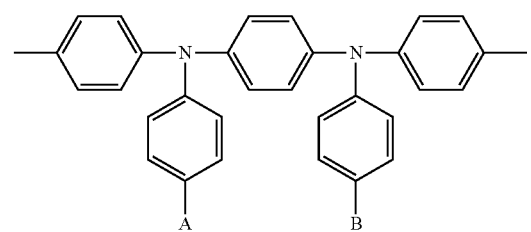

4

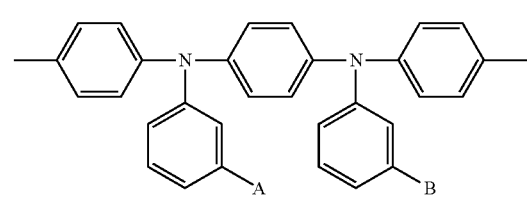

5

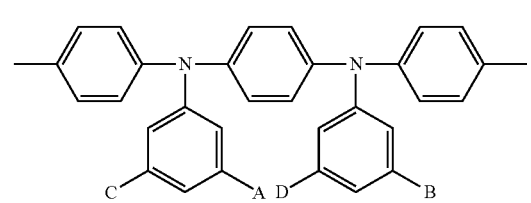

6 wherein X, Y, A, B, C and D are independently selected from H or a substituent group. More preferably, one or more of X, Y, A, B, C and D is independently selected from the group consisting of optionally substituted, branched or linear alkyl, aryl, perfluoroalkyl, thioalkyl, cyano, alkoxy, heteroaryl, alkylaryl and arylalkyl groups. Most preferably, X, Y, A and B are $C_{1-10}$ alkyl. The aromatic rings in the backbone of the polymer may be linked by a direct bond or a bridging group or bridging atom, in particular a bridging heteroatom such as oxygen or sulfur.

Particularly preferred hole transporting polymers of this type are copolymers of arylene repeat units, in particular fluorene repeat units, and a triarylamine repeat unit.

A copolymer comprising a first repeat unit and heteroarylene repeat unit may be utilised for charge transport or emission. Heteroarylene repeat units may be selected from formulae 7-21:

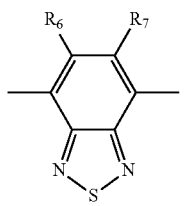

19 wherein $R_6$ and $R_7$ are the same or different and are each independently hydrogen or a substituent group, preferably alkyl, aryl, perfluoroalkyl, thioalkyl, cyano, alkoxy, heteroaryl, alkylaryl or arylalkyl. For ease of manufacture, $R_6$ and $R_7$ are preferably the same. More preferably, they are the same and are each a phenyl group.

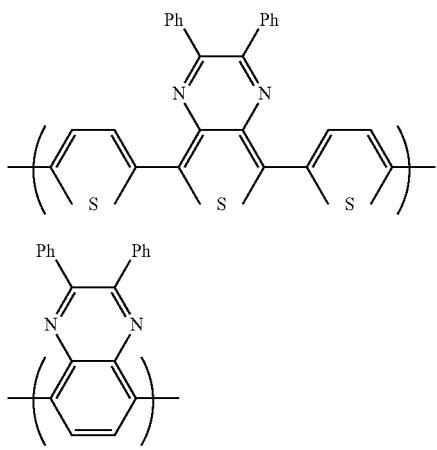

20

21

22

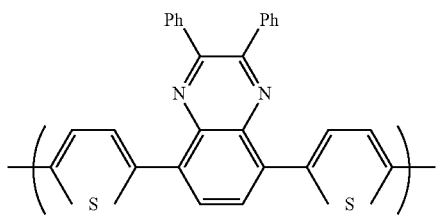

23

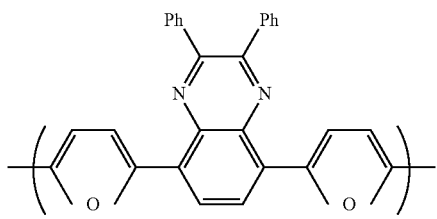

-continued

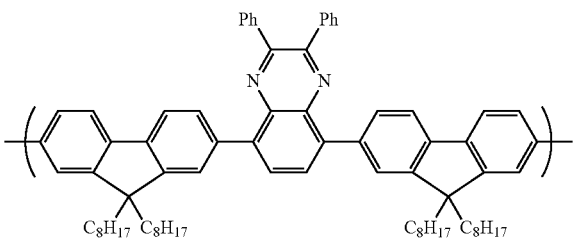

24

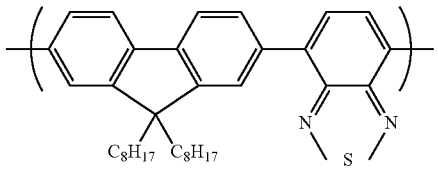

25

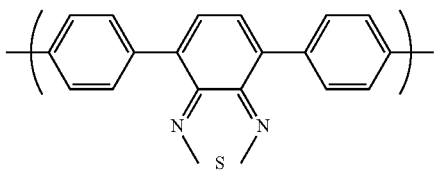

26

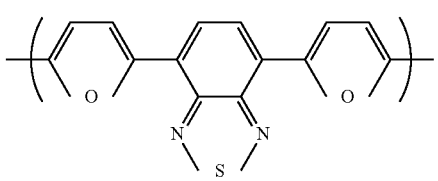

27

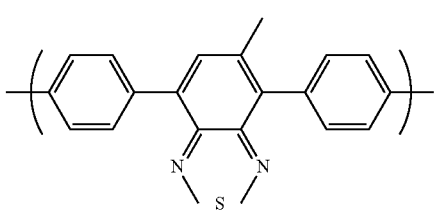

28

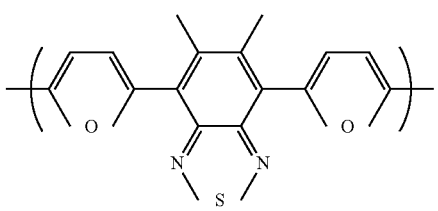

29

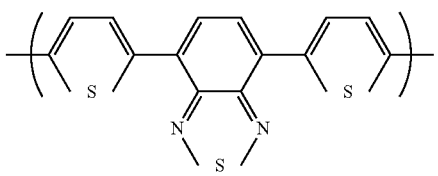

30

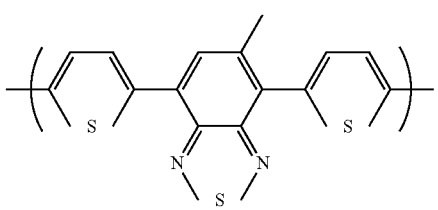

31

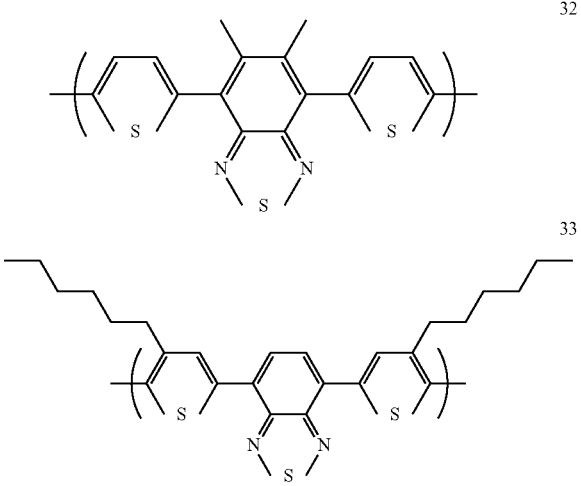

Electroluminescent copolymers may comprise an electroluminescent region and at least one of a hole transporting region and an electron transporting region as disclosed in, for example, WO 00/55927 and U.S. Pat. No. 6,353,083. If only one of a hole transporting region and electron transporting region is provided then the electroluminescent region may also provide the other of hole transport and electron transport functionality.

The different regions within such a polymer may be provided along the polymer backbone, as per U.S. Pat. No. 6,353,083, or as groups pendent from the polymer backbone as per WO 01/62869.

Preferred methods for preparation of these polymers are Suzuki polymerisation as described in, for example, WO 00/53656 and Yamamoto polymerisation as described in, for example, T. Yamamoto, "Electrically Conducting And Thermally Stable π-Conjugated Poly(arylene)s Prepared by Organometallic Processes", Progress in Polymer Science 1993, 17, 1153-1205. These polymerisation techniques both operate via a "metal insertion" wherein the metal atom of a metal complex catalyst is inserted between an aryl group and a leaving group of a monomer. In the case of Yamamoto polymerisation, a nickel complex catalyst is used; in the case of Suzuki polymerisation, a palladium complex catalyst is used.

For example, in the synthesis of a linear polymer by Yamamoto polymerisation, a monomer having two reactive halogen groups is used. Similarly, according to the method of Suzuki polymerisation, at least one reactive group is a boron derivative group such as a boronic acid or boronic ester and the other reactive group is a halogen. Preferred halogens are chlorine, bromine and iodine, most preferably bromine.

It will therefore be appreciated that repeat units and end groups comprising aryl groups as illustrated throughout this application may be derived from a monomer carrying a suitable leaving group.

Suzuki polymerisation may be used to prepare regioregular, block and random copolymers. In particular, homopolymers or random copolymers may be prepared when one reactive group is a halogen and the other reactive group is a boron derivative group. Alternatively, block or regioregular, in particular AB, copolymers may be prepared when both reactive groups of a first monomer are boron and both reactive groups of a second monomer are halogen.

As alternatives to halides, other leaving groups capable of participating in metal insertion include tosylate, mesylate, phenyl sulfonate and triflate.

A single polymer or a plurality of polymers may be deposited from solution to form layer 5. Suitable solvents for polyarylenes include mono- or poly-alkylbenzenes such as toluene and xylene. Particularly preferred solution deposition techniques are spin-coating and inkjet printing.

Spin-coating is particularly suitable for devices wherein patterning of the electroluminescent material is unnecessary—for example for lighting applications or simple monochrome segmented displays.

Inkjet printing is particularly suitable for high information content displays, in particular full colour displays. Inkjet printing of OLEDs is described in, for example, EP 0880303.

If multiple layers of the device are formed by solution processing then the skilled person will be aware of techniques to prevent intermixing of adjacent layers, for example by crosslinking of one layer before deposition of a subsequent layer or selection of materials for adjacent layers such that the material from which the first of these layers is formed is not soluble in the solvent used to deposit the second layer.

Preferred phosphorescent metal complexes comprise optionally substituted complexes of formula (34):

$$ML^1_q L^2_r L^3_s \quad (34)$$

wherein M is a metal; each of $L^1$, $L^2$ and $L^3$ is a coordinating group; q is an integer; r and s are each independently 0 or an integer; and the sum of (a. q)+(b. r)+(c.s) is equal to the number of coordination sites available on M, wherein a is the number of coordination sites on $L^1$, b is the number of coordination sites on $L^2$ and c is the number of coordination sites on $L^3$.

Heavy elements M induce strong spin-orbit coupling to allow rapid intersystem crossing and emission from triplet states (phosphorescence). Suitable heavy metals M include:
lanthanide metals such as cerium, samarium, europium, terbium, dysprosium, thulium, erbium and neodymium; and
d-block metals, in particular those in rows 2 and 3 i.e. elements 39 to 48 and 72 to 80, in particular ruthenium, rhodium, palladium, rhenium, osmium, iridium, platinum and gold.

Suitable coordinating groups for the f-block metals include oxygen or nitrogen donor systems such as carboxylic acids, 1,3-diketonates, hydroxy carboxylic acids, Schiff bases including acyl phenols and iminoacyl groups. As is known, luminescent lanthanide metal complexes require sensitizing group(s) which have the triplet excited energy level higher than the first excited state of the metal ion. Emission is from an f-f transition of the metal and so the emission colour is determined by the choice of the metal. The sharp emission is generally narrow, resulting in a pure colour emission useful for display applications.

The d-block metals form organometallic complexes with carbon or nitrogen donors such as porphyrin or bidentate ligands of formula (35):

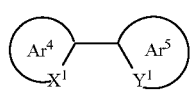

(35)

wherein $Ar^4$ and $Ar^5$ may be the same or different and are independently selected from optionally substituted aryl or heteroaryl; $X^1$ and $Y^1$ may be the same or different and are independently selected from carbon or nitrogen; and $Ar^4$ and $Ar^5$ may be fused together. Ligands wherein $X^1$ is carbon and $Y^1$ is nitrogen are particularly preferred.

Examples of bidentate ligands are illustrated below:

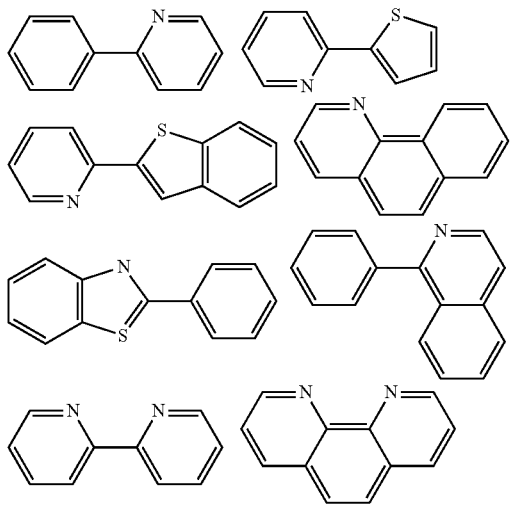

Each of $Ar^4$ and $Ar^5$ may carry one or more substituents. Particularly preferred substituents include fluorine or trifluoromethyl which may be used to blue-shift the emission of the complex as disclosed in WO 02/45466, WO 02/44189, US 2002-117662 and US 2002-182441; alkyl or alkoxy groups as disclosed in JP 2002-324679; carbazole which may be used to assist hole transport to the complex when used as an emissive material as disclosed in WO 02/81448; bromine, chlorine or iodine which can serve to functionalise the ligand for attachment of further groups as disclosed in WO 02/68435 and EP 1245659; and dendrons which may be used to obtain or enhance solution processability of the metal complex as disclosed in WO 02/66552.

Other ligands suitable for use with d-block elements include diketonates, in particular acetylacetonate (acac); triarylphosphines and pyridine, each of which may be substituted.

Main group metal complexes show ligand based, or charge transfer emission. For these complexes, the emission colour is determined by the choice of ligand as well as the metal.

The host material and metal complex may be combined in the form of a physical blend. Alternatively, the metal complex may be chemically bound to the host material. In the case of a polymeric host, the metal complex may be chemically bound as a substituent attached to the polymer backbone, incorporated as a repeat unit in the polymer backbone or provided as an end-group of the polymer as disclosed in, for example, EP 1245659, WO 02/31896, WO 03/18653 and WO 03/22908.

Embodiments of the present invention can also be used as hosts for fluorescent emitters. A wide range of fluorescent low molecular weight metal complexes may be used with the present invention. Suitable ligands for di or trivalent metals include: oxinoids, e.g. with oxygen-nitrogen or oxygen-oxygen donating atoms, generally a ring nitrogen atom with a substituent oxygen atom, or a substituent nitrogen atom or oxygen atom with a substituent oxygen atom such as 8-hydroxyquinolate and hydroxyquinoxalinol-10-hydroxybenzo (h) quinolinato (II), benzazoles (III), schiff bases, azoindoles, chromone derivatives, 3-hydroxyflavone, and carboxylic acids such as salicylato amino carboxylates and ester carboxylates. Optional substituents include halogen, alkyl, alkoxy, haloalkyl, cyano, amino, amido, sulfonyl, carbonyl, aryl or heteroaryl on the (hetero) aromatic rings which may modify the emission colour.

While this invention has been particularly shown and described with reference to preferred embodiments thereof, it will be understood by those skilled in the art that various changes in form and details may be made therein without departing from the scope of the invention as defined by the appended claims.

Examples 2,4,6-tris(4'-bromophenyl)-1,3,5-triazine(1)

A 1 L three-necked round bottomed flask was fitted with a magnetic stirrer, a reflux condenser with $N_2$ inlet bubbler, and a 500 ml pressure-equalizing dropping funnel. The flask was charged with trifluoromethane sulfonic acid (60 g, 35 ml) that was stirred at room temperature. In a separate flask 4-bromobenzonitrile (36.4 g, 0.20 mol) was dissolved in anhydrous $CHCl_3$ (500 ml) and the solution transferred into the dropping funnel under $N_2$ via cannula. The benzonitrile solution was added dropwise and then the reaction mixture was heated to reflux at 90-95° C. for 20-24 hours. The reaction mixture was allowed to cool before cautiously adding to stirred dilute aqueous ammonia solution (250 ml, 3%) cooled in an ice-bath. The product precipitated as an off-white solid and was collected by filtration and washed with $H_2O$ and $Et_2O$. The product was recrystallised from refluxing toluene to give pure product (100% by HPLC). Yield 24.0 g, 66%.

2,4,6-tris(4''-tert-butylbiphenyl)-1,3,5-triazine(2)

(1) (24.0 g, 44 mmol), 4-$^t$Bu-phenyl(pinacol) boronate (38.9 g, 150 mmol) and $Pd(PPh_3)_4$ (4.56 g, 3.95 mmol) were placed in 3 L multineck round bottomed flask fitted with a large stirrer bar and reflux condenser with a $N_2$ inlet bubbler. The apparatus was purged with $N_2$ and toluene (1.5 L) degassed by sparging with $N_2$ was transferred into the reaction vessel via cannula. The mixture was stirred and $Et_4NOH$ (155 ml, 20 wt % aq.) was degassed and added. The reaction was heated to reflux at 115° C. for 44 hours. The reaction was monitored by TLC (20% DCM/hexane) and was stopped when judged to be complete. After the mixture had cooled to room temperature the organic and aqueous layers were separated. The organic layer was washed with HCl (600 ml, 10%) and $H_2O$ (2×600 ml). The collected organic layer was dried over $MgSO_4$, filtered and reduced to dryness in vacuo to give the crude product. The product was recrystallised twice from refluxing dichloromethane/methanol to give good purity (99.84% by HPLC). Yield 13.0 g, 42%

2,4,6-tris(4'-bromo-3'-methylphenyl)-1,3,5-triazine (3)

From 4-bromo-3-methylbenzonitrile in an analogous method to (1). The compound was purified by recrystallisation from dichloromethane/methanol.

2,4,6-tris(4''-tert-butyl-3'-methylbiphenyl)-1,3,5-triazine(4)

By reaction of (3) in an analogous method to (2). The compound was purified by repeated recrystallisation from toluene.

2,4-bis(4'-bromophenyl)-6-phenyl-1,3,5-triazine(5)

$AlCl_3$ (8.68 g, 65.1 mmol) and $NH_4Cl$ (10.45 g, 195 mmol) were place in a 250 ml multineck round bottomed flask fitted with a stirrer bar and reflux condenser with N2 inlet bubbler. The apparatus was purged with $N_2$. 4-Bromobenzonitrile (20 g, 110 mmol) and benzoyl chloride (7.94 g, 56 mmol) were added to the reaction vessel and the flask was heated at 150° C. allowing the molten contents to stir. The stirred mixture evolved HCl gas forming a slurry and then resolidified. Heating was continued for 20 hours. The product was obtained by extracting the mixture in refluxing toluene and recrystallisation from refluxing toluene.

2,4-bis(4''-tert-butylbiphenyl)-6-phenyl-1,3,5-triazine(6)

By reaction of (5) in an analogous method to (2). The compound was purified by column chromatography (10% dichloromethane/hexane).

Device Example

Onto a glass substrate comprising an ITO electrode was deposited, in sequence, a layer of PEDOT/PSS (available from H C Starck of Leverkusen, Germany as Baytron P®); a hole transport layer comprising a copolymer of fluorene and triarylamine repeat units; an emissive layer comprising compound (6) as a host material and the green-emitting iridium-cored dendrimer illustrated below, and as disclosed in WO 02/066552; and a cathode comprising a layer of barium oxide (5 nm) and thick capping layer of aluminium. All layers were deposited by spin-coating from solution.

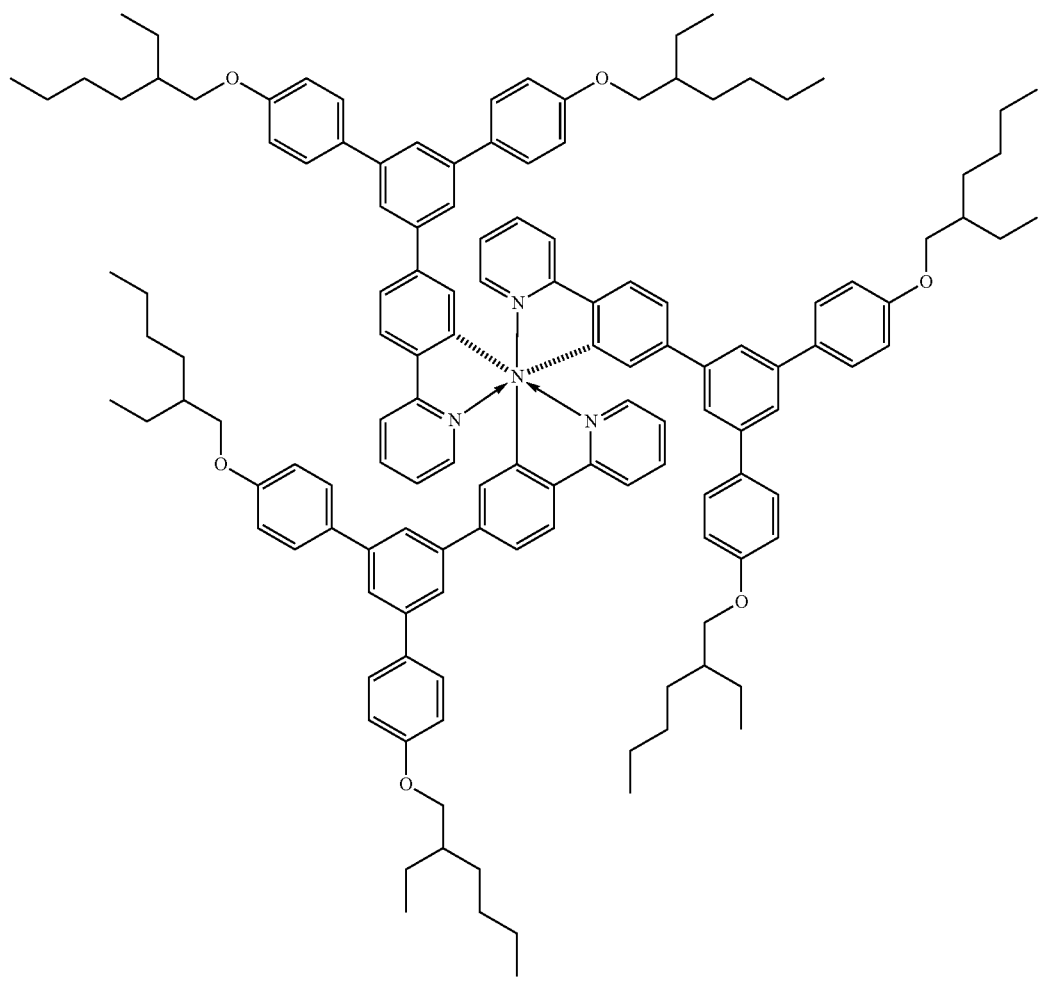

Comparative Device Example

For the purpose of comparison, a device was prepared as per the Device Example above except that a solution processable version of the commonly used host material 4,4'-di (N-carbazole) biphenyl (CBP) was used in place of the solution processable triazine host material (6). CBP was rendered solution processable by substitution with alkyl groups.

The invention claimed is:
1. A method of fabricating an opto-electrical device, the method comprising:
  forming a hole transporting layer over a substrate comprising a first electrode for injecting charge carriers of a first polarity, forming thereover a light-emitting layer by depositing a solution comprising an organic solvent, a solution processable triazine host material and a phosphorescent moiety, and depositing thereover a second electrode for injecting charge carriers of a second polarity opposite to the first polarity, wherein the triazine host material is a small molecule compound and is soluble to a concentration of above 8 mg/ml, wherein the HOMO level of the triazine host material is lower than the HOMO level of the phosphorescent moiety wherein the second electrode has a work function in the range of 2.6 eV to 3.2 eV, and wherein the hole transporting layer comprises a polymer comprising a triarylamine repeat unit and is located between the substrate and the light-emitting layer.

2. A method according to claim 1 wherein the solvent is selected from xylene, toluene, chlorobenzene, chloroform, and tetrahydrofuran.

3. A method according to claim 1, wherein the triazine host material is a triaryltriazine compound and at least one of the aryl groups is a phenyl ring.

4. A method according to claim 3, wherein two or three of the aryl groups have $C_4$-$C_{20}$ alkyl chain solubilizing substituents bonded thereto.

5. A method according to claim 1, wherein the triazine host material has the formula:

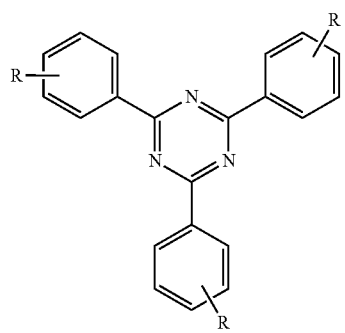

where the R groups are $C_4$-$C_{20}$ alkyl chain solubilizing substituents which may be the same or different.

6. A method according to claim 1, wherein the triazine host material has one of the following formulas:

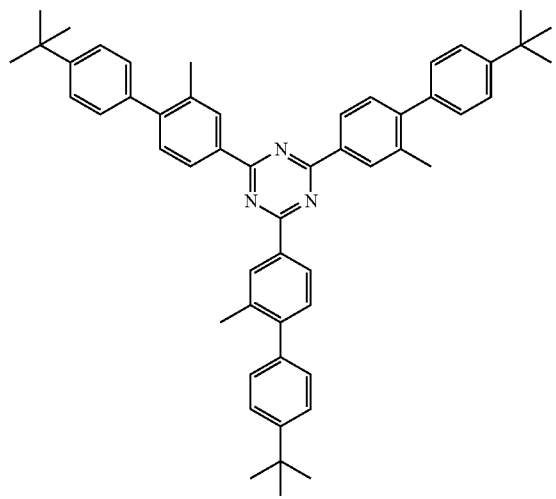

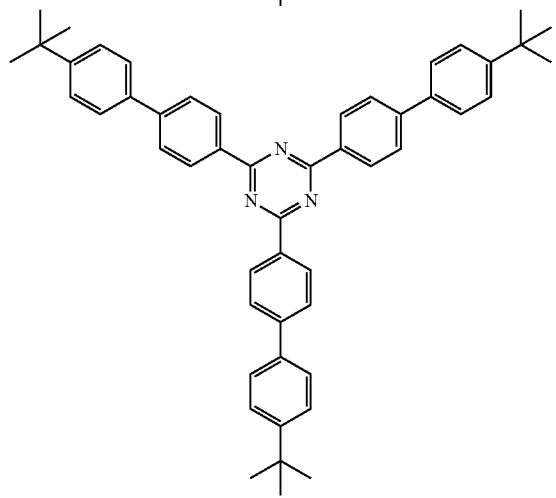

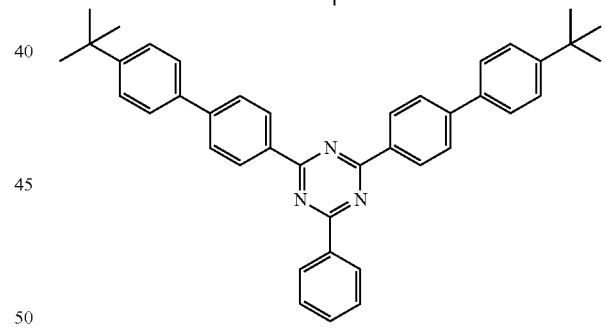

7. A method according to claim 1, wherein the phosphorescent moiety is provided as a separate chemical entity to the solution processable triazine host material and is blended with the solution processable triazine host material.

8. A method according to claim 1, wherein the phosphorescent moiety is chemically bound to the solution processable triazine host material.

9. A method according to claim 1, wherein the phosphorescent moiety is a green emitter.

10. A method according to claim 1, wherein the hole transporting layer has a HOMO level around 4.8-5.5 eV.

* * * * *